(12) United States Patent
Dounay et al.

(10) Patent No.: US 8,487,104 B2
(45) Date of Patent: Jul. 16, 2013

(54) KAT II INHIBITORS

(75) Inventors: Amy B Dounay, Ledyard, CT (US); Christopher J Helal, Mystic, CT (US); Jamison B Tuttle, Westbrook, CT (US); Patrick R Verhoest, Old Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 13/307,140

(22) Filed: Nov. 30, 2011

(65) Prior Publication Data
US 2012/0142729 A1    Jun. 7, 2012

Related U.S. Application Data

(60) Provisional application No. 61/418,791, filed on Dec. 1, 2010, provisional application No. 61/419,232, filed on Dec. 2, 2010.

(51) Int. Cl.
*C07D 215/58*    (2006.01)

(52) U.S. Cl.
USPC .......................................... 546/155; 514/312

(58) Field of Classification Search
None
See application file for complete search history.

(56) References Cited

U.S. PATENT DOCUMENTS 8,183,238 B2 *   5/2012   Claffey et al. ............. 514/235.2
2012/0302599 A1  11/2012   Dounay et al.

FOREIGN PATENT DOCUMENTS

WO    WO 2009064836    5/2009
WO    WO 2010146488   12/2010

OTHER PUBLICATIONS

Ahn, K., et al., Discovery and Characterization of a Highly Selective FAAH Inhibitor that Reduces Inflammatory Pain, *Chemistry & Biology*, vol. 16, 411-420 (2009).
Bundgaard, H., Design of Prodrugs (Elsevier, 1985).
Davis, A., et al., Synthesis and Microbiological Properties of Some Substituted Derivatives of 3-Amino-3,4-dihydroxycarbostyril, *Journal of Medicinal Chemistry*, vol. 18, No. 7, 752-755, (1975).
DiNatale, B., et al., Kynurenic Acid Is a Potent Endogenous Aryl Hydrocarbon Receptor Ligand that Synergistically Induces Interleukin-6 in the Presence of Inflammatory Signaling, *Toxicological Sciences*, vol. 115, No. 1, 89-97 (2010).
Finnin and Morgan, Transdermal Penetration Enhancers: Applications, Limitations, and Potential, *Journal of Pharmaceutical Sciences*, vol. 88, No. 10, 955-958 (1999).
Higuchi, T and Stella, W., Bioreversible Carriers in Drug Design, Pergamon Press, 1987 Ed. E. B. Roche, American Pharmaceutical Association.
Higuchi, T., et al., Pro-drugs as Novel Delivery Systems, vol. 14, ACS Symposium Series (American Chemical Society: Washington, DC, 1975).
Hoover, John E., Remington's Pharmaceutical Sciences, Mack Publishing Co., Easton, Pennsylvania (1975).
Kessler, M., et al., A Glycine Site Associated with N-Methyl-D-Aspartic Acid Receptors: Characterization and Identification of a New Class of Antagonists, *Journal of Neurochemistry*, vol. 52, No. 4, 1319-1325 (1989).
Kibbe et al., Eds., Handbook of Pharmaceutical Excipients (3rd Ed.), American Pharmaceutical Association, Washington (1999).
Liberman et al., Eds., Pharmaceutical Dosage Forms, Marcel Decker, New York, N.Y. (1980).
Mileni, M., et al., Structure-guided inhibitor design for human FAAH by interspecies active site conversion, *PNAS* vol. 105, No. 35, 12820-12824 (2008).
Morris, R.G.M., et al., The role of NMDA receptors in learning and memory, *The NMDA Receptor*, Oxford university Press, Oxford, 137-151 (1989).
Okuno, E., et al., Measruement of Rat Brain Kynurenine Aminotransferase at Physiological Kynurenine concentrations, *Journal of Neurochem.*, vol. 57, No. 2, 533-540 (1991).
Schwarcz, R., et al., Kynurenic Acid: A Potential Pathogen in Brain Disorders$^\alpha$, *Annals New York Academy of Sciences*, Vo. 648, 140-153 (1992).
Soglia, J., et al., The development of a higher throughput reactive intermediate screening assay incorporating micro-bore liquid chromatography-micro-electrospray ionization-tandem mass spectrometry and glutathione ethyl ester as an in vitro conjugating agent, *Journal of Pharmaceutical and Biomedical Analysis*, vol. 36, 105-116 (2004).
van Zutphen, S., et al., Readily available amino acid building blocks for the synthesis of phosphole-containing peptides, *Tetrahedron Letters*, vol. 48, 2857-2859(2007).

\* cited by examiner

*Primary Examiner* — Janet Andres
*Assistant Examiner* — Timothy R Rozof
(74) *Attorney, Agent, or Firm* — Feng Shao

(57) ABSTRACT

The present invention relates to compounds 3-amino-1-hydroxy-2-oxo-1,2,3, 4-tetrahydroquinoline-7-carbonitrile, 3-amino-1-hydroxy-7-(2-methoxyethoxy)-3,4-dihydroquinolin-2(1H)-one, and 3-amino-1-hydroxy-7-[(1S)-2-methoxy-1-methylethoxy]-3,4-dihydroquinolin-2(1H)-one, including racemic mixtures and resolved enantiomers thereof, to pharmaceutically acceptable salts thereof, and to the treatment of cognitive deficits associated with schizophrenia and other psychiatric, neurodegenerative and/or neurological disorders in mammals, including humans.

16 Claims, No Drawings

KAT II INHIBITORS

This application claims the benefit of priority to U.S. provisional patent application Ser. No. 61/418,791 filed Dec. 01, 2010, and to U.S. provisional patent application Ser. No. 61/419,232 filed Dec. 02, 2010, the disclosure of each of which is hereby incorporated by reference in its entirety.

FIELD OF THE INVENTION

The present invention relates to compounds of 3-amino-1-hydroxy-2-oxo-1,2,3,4-tetrahydroquinoline-7-carbonitrile, 3-amino-1-hydroxy-7-(2-methoxyethoxy)-3,4-dihydroquinolin-2(1H)-one, and 3-amino-1-hydroxy-7-[(1S)-2-methoxy-1-methylethoxy]-3,4-dihydroquinolin-2(1H)-one, including racemic mixtures and resolved enantiomers thereof, to pharmaceutically acceptable salts thereof, and to the treatment of cognitive deficits associated with schizophrenia and other psychiatric, neurodegenerative and/or neurological disorders in mammals, including humans.

BACKGROUND OF THE INVENTION

KAT (kynurenine aminotransferase) II is a primary enzyme in the brain for catalyzing the transamination of kynurenine to KYNA (kynurenic acid). (E. Okuno et al., *J. Neurochem.*, vol. 57, 533-540, 1991). KYNA is an effective excitatory amino acid (EAA) receptor antagonist with affinity for the glycine modulatory site of the N-methyl-D-aspartate (NMDA) receptor complex (M. Kessler et al., *J. Neurochem.*, vol. 52, pp. 1319-1328, 1989). As a naturally occurring brain metabolite, KYNA probably serves as a negative endogenous modulator of cerebral glutamatergic function (R. Schwarcz et al., *Ann. N.Y. Acad. Sci.*, vol. 648, pp. 140-153, 1992), and activator of arylhydrocarbon receptors (B. DiNatale et al., *Toxicol. Sci.* vol. 115, pp. 89-97, 2010).

EAA receptors and in particular NMDA receptors are known to play a central role in the function of the mammalian brain (J. C. Watkins and G. L. Collingridge, Eds., *The NMDA Receptor*, Oxford University Press, Oxford, 1989, p. 242). For example, NMDA receptor activation is essential for cognitive processes, such as, for example, learning and memory (Watkins and Collingridge, supra, pp. 137-151). Therefore, reducing KYNA synthesis by inhibition of its synthetic enzyme may enhance EAA signaling and improve cognitive processes, especially in disease states where NMDA hypofunction is anticipated. Thus, there is a need for compounds which act as KAT II inhibitors to reduce KYNA synthesis within the brain to improve cognitive dysfunction in human disease states.

SUMMARY OF THE INVENTION

The present invention provides 3-amino-1-hydroxy-2-oxo-1,2,3,4-tetrahydroquinoline-7-carbonitrile, 3-amino-1-hydroxy-7-(2-methoxyethoxy)-3,4-dihydroquinolin-2(1H)-one, and 3-amino-1-hydroxy-7-[(1S)-2-methoxy-1-methylethoxy]-3,4-dihydroquinolin-2(1H)-one, including racemic mixtures and resolved enantiomers thereof, to pharmaceutically acceptable salts thereof. For brevity, the 3(S) enantiomer will be discussed, but the invention concerns not only the 3(S) enantiomer but both enantiomers and racemic mixtures, including pharmaceutically acceptable salts thereof.

The present invention includes a compound of (3S)-3-amino-1-hydroxy-2-oxo-1,2,3,4-tetrahydroquinoline-7-carbonitrile, which is represented by Formula IA:

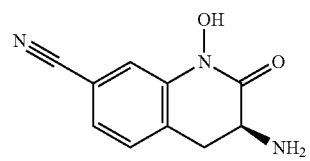

IA

The present invention includes a compound of (3S)-3-amino-1-hydroxy-7-(2-methoxyethoxy)-3,4-dihydroquinolin-2(1H)-one, which is represented by Formula IIA:

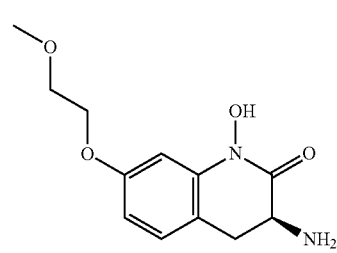

IIA

The present invention includes a compound of (3S)-3-amino-1-hydroxy-7-[(1S)-2-methoxy-1-methylethoxy]-3,4-dihydroquinolin-2(1H)-one, which is represented by Formula IIIA:

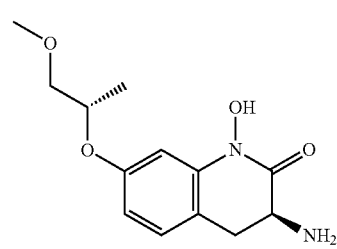

IIIA

This invention also includes pharmaceutically acceptable salts, hydrates, solvates, isomers, crystalline and non-crystalline forms, isomorphs, polymorphs, and metabolites of compounds of Formula I, Formula II, and Formula III. This invention also includes all tautomers and stereochemical isomers of these compounds.

This invention also is directed, in part, to a method for treating a KAT II mediated disorder in a mammal. Such disorders include cognitive deficits associated with schizophrenia and other neurodegenerative and/or neurological disorders. The method comprises administering a compound of Formula I, Formula II, or Formula III or a pharmaceutically acceptable salt thereof, to the mammal in an amount that is therapeutically effective to treat the condition.

DETAILED DESCRIPTION OF THE INVENTION

One embodiment of the present invention is a compound of Formula I, Formula IA or Formula IB:

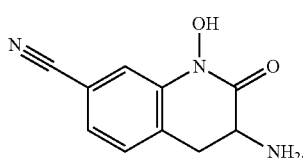

I

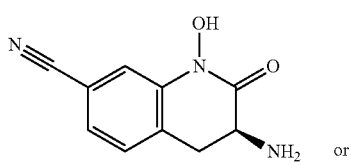

IA

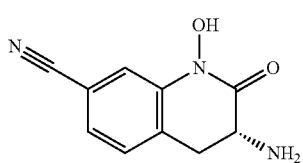

IB

As used herein "compounds of the invention" include compounds of Formula I, Formula II, and Formula III. Such terms are also defined to include all forms of the compounds of Formula I, Formula II, and Formula III, including racemic mixtures, enantiomers, hydrates, solvates, isomers, crystalline and non-crystalline forms, isomorphs, polymorphs, and metabolites thereof.

Another embodiment of the present invention is an enantiomerically pure compound of Formula IA, Formula IIA, and Formula IIIA having at least 95% enantiomeric excess at the amino-substituted carbon. Another aspect of this invention includes an enantiomerically pure compound of Formula IA, Formula IIA, and Formula IIIA having at least 99% enantiometic excess (ee) at the amino-substituted carbon.

Another embodiment of the present invention is a compound of Formula II, Formula IIA or Formula IIB:

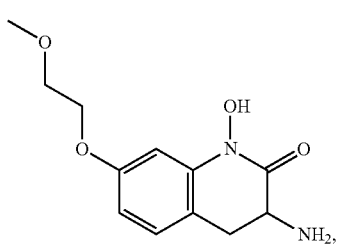

II

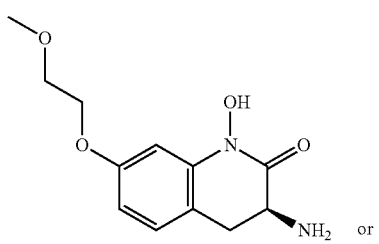

IIA

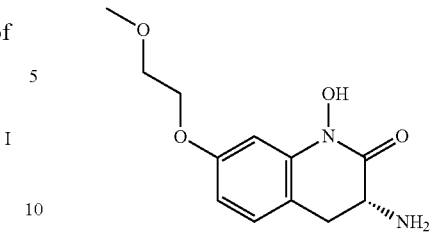

IIB

Another embodiment of the present invention is a compound of Formula III, Formula IIIA or Formula IIIB:

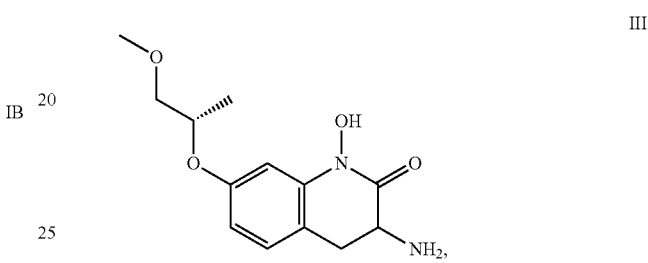

III

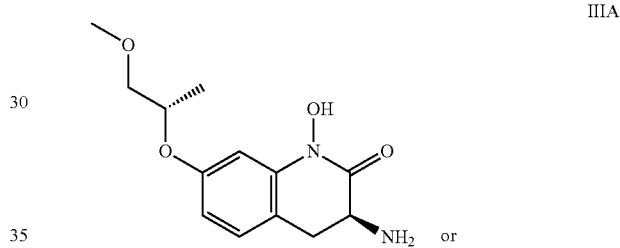

IIIA

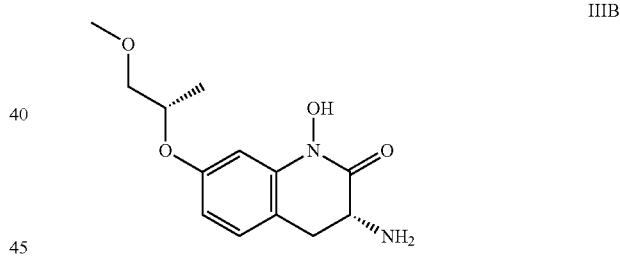

IIIB

Another embodiment of the present invention is the process to make the compounds of the invention, including the enantiomerically pure compounds of Formula IA, IIA, and IIIA having at least 95% ee at the amino-substituted carbon or also having at least 99% ee at the amino-substituted carbon.

Another embodiment of the present invention is a method for or preparation of a medicament for the treatment or prevention in a mammal of a condition selected from the group consisting of acute neurological and psychiatric disorders; stroke; cerebral ischemia; spinal cord trauma; cognitive impairment, including mild cognitive impairment; head trauma; perinatal hypoxia; cardiac arrest; hypoglycemic neuronal damage; dementia; Alzheimer's disease; Huntington's Chorea; amyotrophic lateral sclerosis; ocular damage; retinopathy; cognitive disorders; idiopathic and drug-induced Parkinson's disease; muscular spasms and disorders associated with muscular spasticity including tremors; epilepsy; convulsions; migraine; urinary incontinence; substance tolerance; substance withdrawal; psychosis; schizophrenia; negative symptoms associated with schizophrenia; autism, including autism spectrum disorders; bipolar disorder; depression, including but not limited to Major Depressive Disorder and treatment-resistant depression; cognitive impairment associated with depression; cognitive impairment associated with cancer therapy; anxiety; mood disorders; inflammatory disorders; sepsis; cirrhosis; cancer and/or tumors associated with immune response escape; trigeminal neuralgia; hearing loss; tinnitus; macular degeneration of the eye; emesis; brain edema; pain; tardive dyskinesia; sleep disorders; attention deficit/hyperactivity disorder; attention deficit disorder; disorders that comprise as a symptom of deficiency in attention and/or cognition; and conduct disorder; comprising administering a compound selected from a compound of Formula I, IA, IB, II, IIA, IIB, III, IIIA, or IIIB.

Another embodiment of the present invention is a method for or preparation of a medicament for the treatment or prevention in a mammal of a condition selected from the group consisting of dementia; cognitive deficit symptoms of Alzheimer's disease; attention deficit symptoms of Alzheimer's disease; multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder (e.g., reading disorder, mathematics disorder, or a disorder of written expression); attention-deficit/hyperactivity disorder; age-related cognitive decline; cognitive deficits associated with psychoses; or cognitive deficits associated with schizophrenia, comprising administering a compound selected from a compound of Formula I, IA, IB, II, IIA, IIB, III, IIIA, or IIIB.

Isomers

When an asymmetric center is present in a compound of Formula I, Formula II, or Formula III, hereinafter referred to as the compounds of the invention, the compound may exist in the form of optical isomers (enantiomers). In one embodiment, the present invention comprises enantiomers and mixtures, including racemic mixtures of the compounds of the present invention. In another embodiment, for compounds of the present invention that contain more than one asymmetric center, the present invention comprises diastereomeric forms (individual diastereomers and mixtures thereof) of compounds.

Tautomeric Forms

The present invention comprises the tautomeric forms of compounds of of the present invention. Where structural isomers are interconvertible via a low energy barrier, tautomeric isomerism ('tautomerism') can occur. This can take the form of proton tautomerism in compounds of the present invention containing, for example, an imino, keto, or oxime group, or so-called valence tautomerism in compounds which contain an aromatic moiety. It follows that a single compound may exhibit more than one type of isomerism. The various ratios of the tautomers in solid and liquid form is dependent on the various substituents on the molecule as well as the particular crystallization technique used to isolate a compound.

Salts

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining compounds of of the present invention with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclylic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sulfanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diethanolamine, glycine, lysine, meglumine, ethanolamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (i.e., decyl, lauryl, myristyl, and stearyl chlorides, bromides, and iodides), arylalkyl halides (i.e., benzyl and phenethyl bromides), and others.

In one embodiment, hemisalts of acids and bases may also be formed, for example, hemisulphate and hemicalcium salts.

Isotopes

The present invention also includes isotopically labeled compounds, which are identical to those recited in the compounds of the present invention, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out the procedures disclosed in the Schemes and/or in the Examples and Preparations below, by substituting a readily available isotopically labeled reagent for a non-isotopically labeled reagent.

The invention also relates to prodrugs of the compounds of Formula I, IA, IB, II, IIA, IIB, III, IIIA, or IIIB. Thus certain derivatives of compounds of Formula I, IA, IB, II, IIA, IIB, III, IIIA, or IIIB which may have little or no pharmacological activity themselves can, when administered into or onto the body, be converted into compounds of Formula I, IA, IB, II, IIA, IIB, III, IIIA, or IIIB having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I, IA, IB, II, IIA, IIB, III, IIIA, or IIIB with certain moieties known to those skilled in the art as 'pro-moieties' as described, for example, in Design of Prodrugs by H. Bundgaard (Elsevier, 1985).

Some non-limiting examples of prodrugs in accordance with the invention include:

(i) where the compound of Formula I, IA, IB, II, IIA, IIB, III, IIIA, or IIIB contains a carboxylic acid functionality which is functionalized into a suitably metabolically labile group (esters, carbamates, etc.) on the compound of Formula I, IA, IB, II, IIA, IIB, III, IIIA, or IIIB;

(ii) where the compound of Formula I, IA, IB, II, IIA, IIB, III, IIIA, or IIIB contains an alcohol functionality which is functionalized into a suitably metabolically labile group (esters, carbonates, carbamates, acetals, ketals, etc.) on the compound of Formula I, IA, IB, II, IIA, IIB, III, IIIA, or IIIB; and (iii) where the compound of Formula I, IA, IB, II, IIA, IIB, III, IIIA, or IIIB contains a primary or secondary amino functionality, or an amide which is functionalized into a suitably metabolically labile group, e.g., a hydrolyzable group (amides, carbamates, ureas, phosphonates, sulfonates, etc.) on the compound of Formula I, IA, IB, II, IIA, IIB, III, IIIA, or IIIB.

Further examples of replacement groups in accordance with the foregoing examples and examples of other prodrug types may be found in the aforementioned references.

Moreover, certain compounds of Formula I, IA, IB, II, IIA, IIB, III, IIIA, or IIIB may themselves act as prodrugs of other compounds of Formula I, IA, IB, II, IIA, IIB, III, IIIA, or IIIB.

Administration and Dosing

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

Use in the Preparation of a Medicament

In another embodiment, the invention comprises the use of one or more compounds of the invention for the preparation of a medicament for the treatment of the conditions recited herein.

Pharmaceutical Compositions

For the treatment of the conditions referred to herein, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of of the present invention are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (i.e., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

Co-Administration

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

In one embodiment, the compounds of this invention are administered as adjunctive therapy with known anti-psychotics such as Ziprasidone (Geodon), Clozapine, Molindone, Loxapine, Pimozide, Risperidone, Olanzapine, Remoxipride, Sertindole, Amisulpride, Quetiapine, Prochlorperazine, Fluphenazine, Trifluoperazine, Thioridazine, Haloperidol, Chlorpromazine, Flupentixol and Pipotiazine.

In another embodiment, the compounds of the present invention may also be used in combination with CNS agents such as antidepressants (such as sertraline), anti-Parkinsonian drugs (such as deprenyl, L-dopa, Requip, Mirapex, MAOB inhibitors such as selegiline and rasagiline, comT inhibitors such as Tasmar, A-2 inhibitors, dopamine reuptake inhibitors, NMDA antagonists, Nicotine agonists, Dopamine agonists and inhibitors of neuronal nitric oxide synthase), anti-Alzheimer's drugs such as donepezil, tacrine, alpha2delta inhibitors, COX-2 inhibitors, gaba pentenoids, propentofylline or metrifonate, and antipyschotics such as PDE10 inhibitors, 5HT2C agonists, alpha 7 nicotinic receptor agonists, CB1 antagonists and compounds having activity antagonizing dopamine D2 receptors.

Kits

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

Intermediates

In another embodiment, the invention relates to the novel intermediates useful for preparing the compounds of the invention.

Experimental Procedures and Working Examples

The following Examples illustrate the present invention. It is to be understood, however, that the invention, as fully described herein and as receited in the claims, is not intended to be limited by the details of the following Examples.

The following abbreviations are used herein:

brine: saturated aqueous sodium chloride solution

| | |
|---|---|
| EtOAc: | ethyl acetate |
| min: | minutes |
| psi: | Pounds per square inch |
| RT: | room temperature |

Experimental Procedures

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluants/gradients were chosen to provide appropriate $R_f$s or retention times.

EXAMPLES

Example 1

(3S)-3-Amino-1-hydroxy-2-oxo-1,2,3,4-tetrahydroquinoline-7-carbonitrile, HCl Salt (1)

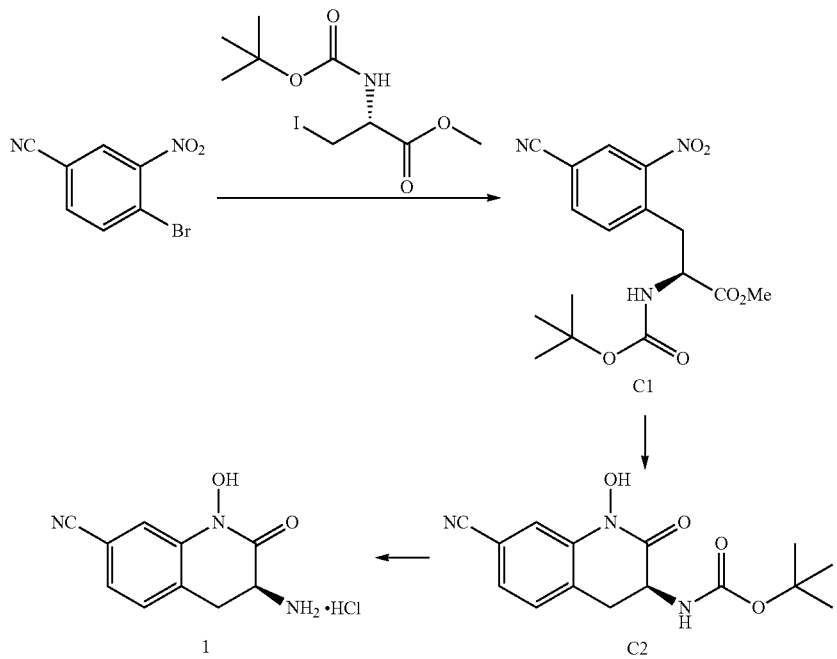

Step 1. Synthesis of methyl N-(tert-butoxycarbonyl)-4-cyano-2-nitro-L-phenylalaninate (C1). A 3-necked, 2-liter round-bottomed flask equipped with a mechanical stirrer and temperature probe was charged with zinc powder (86.41 g, 1.32 mol). N,N-Dimethylformamide (500 mL) was added and the flask was cooled in a water bath at 10 to 12° C. Trimethylsilyl chloride (62.73 mL, 493.4 mmol) was added drop-wise while the internal temperature was held at 20 to 25° C., and the resulting suspension was stirred at 18 to 22° C. for 30 minutes. The stirring was stopped and the solids were allowed to settle; the dark yellow supernatant was removed via cannula using suction and then was discarded. To the solid was added N,N-dimethylformamide (250 mL) and the suspension was stirred for 5 minutes. The stirring was stopped and the supernatant was again removed via cannula. This wash process was carried out twice more under identical conditions. N,N-Dimethylformamide (100 mL) was added to the flask to give a suspension of activated zinc.

A solution of methyl N-(tert-butoxycarbonyl)-3-iodo-L-alaninate (which may be prepared according to S. van Zutphen et al., *Tetrahedron Lett.* 2007, 48, 2857-2859) (173.98 g, 528.59 mmol) in N,N-dimethylformamide (500 mL) was added drop-wise via addition funnel to the activated zinc suspension, while cooling the flask in a water bath at 8 to 10° C. The internal temperature was held below 25° C. during the addition. The cooling bath was removed and the mixture was stirred at 20 to 25° C. for 30 minutes. Analysis by thin layer chromatography (4:1 heptane/EtOAc) showed complete conversion of the starting material to the zincate. The stirring was stopped and, after the solids had settled, the organozinc solution was transferred via cannula, using nitrogen gas pressure, into an addition funnel while leaving the solid zinc behind. N,N-Dimethylformamide (100 mL) was added to the zinc residue and the mixture was stirred for 5 minutes. The stirring was stopped and the supernatant was transferred to the addition funnel via cannula in the same manner.

A 4-necked, 5-liter round-bottomed flask equipped with a mechanical stirrer, an addition funnel and a temperature probe was charged with a solution of 4-bromo-3-nitrobenzonitrile (100 g, 440.5 mmol) in N,N-dimethylformamide (1 L). 2-Dicyclohexylphosphino-2',4',6'-triisopropylbiphenyl (XPhos) (21.0 g, 44.0 mmol) and palladium(II) acetate (4.94 g, 22.0 mmol) were added and the flask was cooled in a water bath at 14 to 16° C. The zincate solution that had been transferred to an addition funnel was added as a small stream while the internal temperature was held at 18 to 20° C. The resulting mixture was stirred at 20° C. for 16 hours, at which time EtOAc (1 L) was added and the mixture was filtered through Celite. The Celite pad was washed with EtOAc (500 mL) and to the filtrates were added EtOAc (1 L) and tert-butyl methyl ether (500 mL). The organic phase was washed with 20% brine (3×1 L) and then concentrated to give a dark orange oil. The oil was dissolved in tert-butyl methyl ether (500 mL), filtered through Celite, and the Celite pad was washed with tert-butyl methyl ether (2×100 mL). The filtrates were concentrated to dryness to give a dark brown oil, which was chromatographed on silica (heptane/EtOAc gradient elution) to give a beige solid (178 g), which was slurried in heptane (900 mL) for 16 hours. The solid was filtered, washed with heptane (2×100 mL) and dried under vacuum at 30° C. for 4 hours to provide C1 as an off-white solid. Yield: 94.67 g, 271.0 mmol, 62% yield. $^1$H NMR (400 MHz, CDCl$_3$) δ 1.34 (s, 9H), 3.25 (dd, J=13.4, 8.8 Hz, 1H), 3.65 (dd, J=13.4, 5.5 Hz, 1H), 3.75 (s, 3H), 4.63-4.72 (m, 1H), 5.24 (br d, J=7.9 Hz, 1 H), 7.57 (d, J=8.0 Hz, 1 H), 7.81 (br d, J=8.0 Hz, 1 H), 8.26 (br s, 1H).

Step 2. Synthesis of tert-butyl [(3S)-7-cyano-1-hydroxy-2-oxo-1,2,3,4-tetrahydroquinolin-3-yl]carbamate (C2). A 1-liter Atlantis pressure reactor (Biotage) was charged with 5% sulfided platinum on carbon [Pt(S)/C] (7.00 g) and C1 (70 g, 200 mmol). Pyridine (700 mL) was added and the mixture was hydrogenated at 23° C. under 5 psi of hydrogen gas. After 2 hours the reaction was filtered to remove the catalyst, and the filtrate was concentrated in vacuo to a minimum volume. The residue was coevaporated with heptane (4×500 mL) to remove residual pyridine. The resulting solid was slurried in tert-butyl methyl ether (350 mL) at 20° C. for 16 hours; the slurry was filtered and the solid was washed with tert-butyl methyl ether (2×50 mL) and dried under vacuum at 30° C. for 1 hour to give C2 as an off-white solid (45.75 g). The filtrate was concentrated to give a second crop of C2 (6.08 g). Overall yield: 51.83 g, 170.9 mmol, 85%. $^1$H NMR (400 MHz, DMSO-$d_6$) δ 1.41 (s, 9H), 3.06-3.15 (m, 2H), 4.28-4.37 (m, 1H), 7.30 (d, J=8.7 Hz, 1H), 7.43-7.49 (m, 3H), 10.76 (s, 1H).

Step 3. Synthesis of Example 1. A 3-necked, 2-liter round-bottomed flask equipped with a mechanical stirrer was charged with a solution of HCl in 2-propanol (5-6 M, 1.05 L). To the flask was added C2 (53.13 g, 175.2 mmol) in one portion, and the mixture was stirred at 20° C. After 1.5 hours, the thick suspension was filtered and the solid was washed with 2-propanol (100 mL) and diethyl ether (2×100 mL), then dried under vacuum at 30° C. for 16 hours to afford Example 1 as a white solid. Yield: 41 g, 170 mmol, 97%. $^1$H NMR (400 MHz, DMSO-$d_6$) δ 3.21 (dd, J=15.2, 14.6 Hz, 1H), 3.33 (dd, J=15.6, 6.5 Hz, 1H, assumed; partially obscured by solvent peak), 4.47 (dd, J=14.5, 6.5 Hz, 1H), 7.56-7.58 (m, 2H), 7.59-7.60 (m, 1H), 8.75 (br s, 3H), 11.16 (br s, 1H). HPLC retention time: 1.347 minutes (Column: Waters Atlantis T3, 3.0×75 mm, 3 μm; Mobile phase A: 0.05% trifluoroacetic acid in water; Mobile phase B: 0.05% trifluoroacetic acid in acetonitrile; Gradient: 5% to 95% B over 10 min; Flow rate: 1.2 mL/min).

Example 2

(3S)-3-Amino-1-hydroxy-7-[(1S)-2-methoxy-1-methylethoxy]-3,4-dihydroquinolin-2(1H)-one, HCl Salt (2)

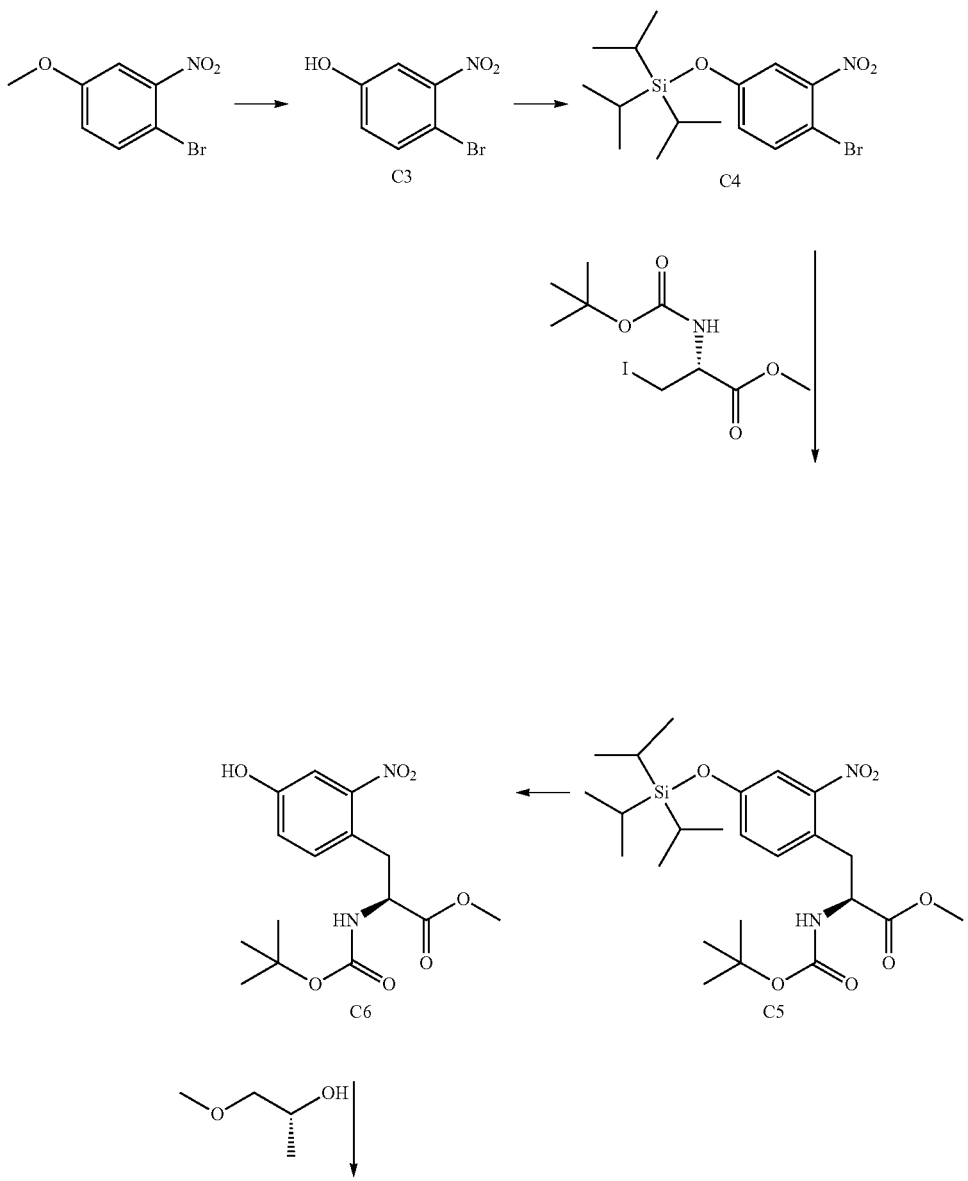

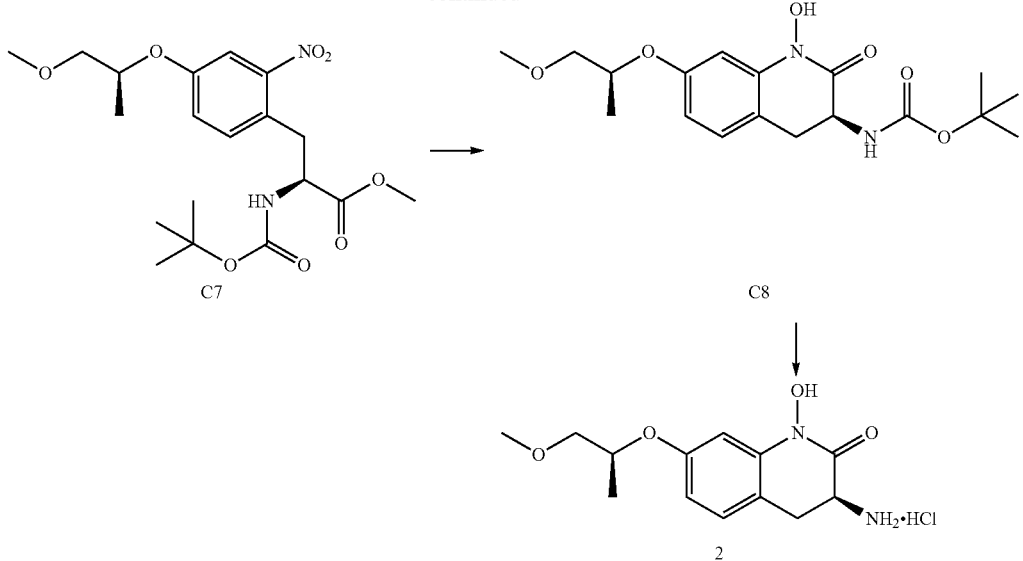

Step 1. Synthesis of 4-bromo-3-nitrophenol (C3). 1-Bromo-4-methoxy-2-nitrobenzene (170 g, 0.73 mol) was dissolved in dichloromethane (1.5 L) in a 5-liter, 3-necked flat-bottomed flask equipped with a thermometer, pressure-equalizing dropping funnel and exhaust gas scrubber (1 M aqueous sodium hydroxide). The solution was cooled to −78° C. under argon. Boron tribromide (176 mL, 1.86 mol) was dissolved in cold dichloromethane (1.6 L, 0° C.); this was added to the cooled reaction via the dropping funnel over 2 hours. An exotherm brought the temperature to −55° C. At the completion of the addition, the cooling bath was removed and the reaction was allowed to warm to RT and stir for 48 hours.

The reaction mixture was added to cold water (2.0 L, ice/water bath) over 4 hours via a dropping funnel, maintaining the internal temperature below 20° C. A scrubber (1 M aqueous sodium hydroxide) was used to prevent release of the HBr gas that was formed. The quenched mixture was stirred at RT for an additional hour, at which time the phases were separated and the aqueous layer was extracted with EtOAc (2.0 L); the combined organic layers (dichloromethane and EtOAc) were washed with saturated aqueous sodium bicarbonate solution (2×1.2 L; lower phase was the organic layer), then with brine (1 L, lower phase was the aqueous layer), dried over magnesium sulfate and concentrated in vacuo. The residue was suspended in dichloromethane (320 mL) and slurried overnight, and the solid was collected by filtration. The solid was dissolved in aqueous sodium hydroxide solution (2.0 M, 500 mL) and extracted with dichloromethane (500 mL). The dichloromethane layer was then extracted with aqueous sodium hydroxide solution (250 mL), and the combined aqueous layers were acidified to pH 2 with aqueous HCl (1.0 M, 790 mL). The precipitated phenol was filtered and dried under vacuum at 40° C. for 18 hours to provide C3 as a solid. Yield: 125.5 g, 0.5757 mol, 79%. $^1$H NMR (400 MHz, CD$_3$OD) δ 6.95 (dd, J=8.8, 2.9 Hz, 1H), 7.24 (d, J=2.9 Hz, 1H), 7.57 (d, J=8.8 Hz, 1H).

Step 2. Synthesis of (4-bromo-3-nitrophenoxy)(triisopropyl)silane (C4). Triisopropylsilyl chloride (182 mL, 0.850 mol) was added in one portion to a solution of C3 (169 g, 0.775 mol) and imidazole (105 g, 1.54 mol) in N,N-dimethylformamide (845 mL). The reaction was stirred for 18 hours at RT, then was poured into water (2 L). After extraction with tert-butyl methyl ether (1 L), the organic phase was washed with water (3×2 L), then with brine (1 L), dried over magnesium sulfate and concentrated in vacuo to an oil. This was purified by chromatography on silica gel (Gradient: 0% to 5% EtOAc in heptane) to provide C4. Yield: 279 g, 0.745 mol, 96%. $^1$H NMR (400 MHz, CDCl$_3$) δ 1.11 (d, J=7.1 Hz, 18H), 1.22-1.33 (m, 3H), 6.95 (dd, J=8.8, 2.9 Hz, 1H), 7.35 (d, J=2.9 Hz, 1H), 7.55 (d, J=8.7 Hz, 1H).

Step 3. Synthesis of methyl N-(tert-butoxycarbonyl)-2-nitro-O-(triisopropylsilyl)-L-tyrosinate (C5). The following zincate formation was carried out in two batches due to the exotherm observed during this reaction. Dry degassed N,N-dimethylformamide (32 mL) was added to zinc (10.5 g, 0.161 mol) in a straight-sided vessel under argon. Trimethylsilyl chloride (4.05 mL, 31.9 mmol) was added and the mixture was stirred vigorously for 30 minutes, at which time the stirring was stopped and the zinc was allowed to settle. The supernatant was decanted under a flow of argon, and N,N-dimethylformamide (20 mL) was added to the zinc. The mixture was stirred for 30 seconds, the zinc was allowed to settle, and the supernatant was removed as before. This procedure was repeated twice more. A solution of methyl N-(tert-butoxycarbonyl)-3-iodo-L-alaninate (which may be prepared according to S. van Zutphen et al., *Tetrahedron Lett.* 2007, 48, 2857-2859) (22.86 g, 69.46 mmol) in N,N-dimethylformamide (55 mL) was added to the activated zinc and the mixture was stirred vigorously. After the exotherm had subsided (this was controlled with an ice bath), the reaction was stirred for an additional 30 minutes, at which time the stirring was stopped and the zinc was allowed to settle. The supernatants from both zincate formations were decanted under a flow of argon into a clean reaction flask. A solution of C4 (40.0 g, 106.9 mmol) in N,N-dimethylformamide (100 mL), palladium(II) acetate (1.20 g, 5.34 mmol) and 2-dicyclohexylphosphino-2',4',6'-triisopropylbiphenyl (XPhos) (5.10 g, 10.70 mmol) were added sequentially to the zincate. The reaction was heated at 40° C. for 18 hours, then was poured into water (400 mL); EtOAc (400 mL) was added, and the resulting mixture was filtered through a pad of Celite and the filter cake was washed with EtOAc (2×100 mL). The layers were separated and the aqueous layer was extracted with EtOAc (100 mL); the combined organic layers were washed with brine (5×400 mL), dried over magnesium sulfate, filtered, and concentrated in vacuo. Purification using silica gel chromatography (Gradient: 2% to 10% EtOAc in heptane) afforded C5 as a pale orange oil that solidified on standing. Yield: 44.3 g, 89.2 mmol, 83%. $^1$H NMR (400 MHz, CDCl$_3$) δ 1.10 (d, J=7.2 Hz, 18H), 1.23-1.31 (m, 3H), 1.37 (s, 9H), 3.19 (dd, J=13.5, 8.2 Hz, 1H), 3.41 (dd, J=13.7, 5.8 Hz, 1H), 3.71 (s, 3H), 4.56-4.66 (m, 1H), 5.18 (br d, J=8 Hz, 1H), 7.05 (dd, J=8.4, 2.6 Hz, 1H), 7.21 (d, J=8.5 Hz, 1H), 7.43-7.47 (m, 1H).

Step 4. Synthesis of methyl N-(tert-butoxycarbonyl)-2-nitro-L-tyrosinate (C6). Tetrabutylammonium fluoride (1 M solution in tetrahydrofuran, 228.1 mL, 228.1 mmol) was added to a solution of C5 (103 g, 207 mmol) in tetrahydrofuran (1.0 L) under argon. The reaction was stirred for 15 minutes. The reaction mixture was concentrated in vacuo, then partitioned between EtOAc (400 mL) and 10% aqueous citric acid solution (400 mL). The layers were separated and the aqueous layer was extracted with EtOAc (200 mL). The combined organic layers were washed with 10% aqueous citric acid solution (300 mL), then with water (300 mL) and with brine (300 mL), dried over magnesium sulfate, and concentrated under reduced pressure to provide a brown oil, which was triturated with heptane. The resulting solid was collected by filtration, washed with heptane, and dried under vacuum at 70° C. to provide C6 as a beige solid. Yield: 50.6 g, 149 mmol, 72% yield. LCMS m/z 339.1 (M−1). $^1$H NMR (400 MHz, CD$_3$OD) δ 1.35 (s, 9H), 2.99 (dd, J=13.7, 9.6 Hz, 1H), 3.43 (dd, J=13.7, 5.6 Hz, 1H), 3.69 (s, 3H), 4.46-4.53 (m, 1H), 6.98-7.0 (m, 1H), 7.01 (dd, J=8.4, 2.6 Hz, 1H), 7.21 (d, J=8.5 Hz, 1H), 7.37 (d, J=2.5 Hz, 1H).

Step 5. Synthesis of methyl N-(tert-butoxycarbonyl)-O-[(1S)-2-methoxy-1-methylethyl]-2-nitro-L-tyrosinate (C7). A solution of diisopropyl azodicarboxylate (92 mL, 0.467 mol) in tetrahydrofuran (500 mL) was added over 30 minutes to a cooled (ice/water bath) solution of C6 (108 g, 0.317 mol), triphenylphosphine (123 g, 0.469 mol) and (2R)-1-methoxypropan-2-ol (42.1 g, 0.467 mol). An exotherm was observed, which increased the reaction temperature from 0 to 25° C. The reaction was stirred for 18 hours at RT, then partitioned between EtOAc (500 mL) and water (500 mL). The aqueous layer was extracted with EtOAc (250 mL), and the combined organic layers were washed with brine (250 mL), dried over magnesium sulfate, and concentrated in vacuo. The residue was suspended in a mixture of diethyl ether and heptane (1:1, 750 mL) and allowed to stand for 18 hours. The solid (a mixture of triphenylphosphine oxide and reduced diisopropyl azodicarboxylate) was removed by filtration, and the filtrate was concentrated in vacuo. Purification via silica gel chromatography (Gradient: 0% to 40% EtOAc in heptane) afforded C7 contaminated with reduced diisopropyl azodicarboxylate (144 g). This mixture could be used in the following step with no detrimental effect on the reaction. $^1$H NMR (400 MHz, CDCl$_3$) δ 1.32 (d, J=6.3 Hz, 3H), 1.37 (br s, 9H), 3.17 (dd, J=13.7, 8.2 Hz, 1H), 3.41 (s, 3H), 3.44 (dd, J=13.7, 5.5 Hz, 1H), 3.51 (dd, half of ABX pattern, J=10.3, 4.0 Hz, 1H), 3.58 (dd, half of ABX pattern, J=10.3, 6.2 Hz, 1H), 3.73 (s, 3H), 4.54-4.66 (m, 2H), 5.19 (br d, J=8.4 Hz, 1H), 7.12 (dd, J=8.6, 2.6 Hz, 1H), 7.25 (d, J=8.5 Hz, 1H), 7.50-7.53 (m, 1H).

Step 6. Synthesis of tert-butyl {(3S)-1-hydroxy-7-[(1S)-2-methoxy-1-methylethoxy]-2-oxo-1,2,3,4-tetrahydroquinolin-3-yl}carbamate (C8). C7 (154 g, 373 mmol) was dissolved in pyridine (770 mL) and split between two 1-liter autoclaves. Platinum on carbon (3%, 7.28 g, 1.13 mmol) was added to each reaction as a paste in water (20 mL). Each autoclave was charged with 16 bar of hydrogen and the reactions were left to stir at RT for 6 hours; an exotherm raised the temperature to 27° C. Thin layer chromatography (Eluant: 1:1 EtOAc/heptane) indicated the presence of starting material, so both autoclaves were re-charged with 16 bar of hydrogen and stirred for 18 hours at RT. The catalyst was removed by filtration through Celite, the filter pads were washed with EtOAc (250 mL) and the filtrates were concentrated under reduced pressure. The residues were dissolved in EtOAc (1 L) and washed with 10% aqueous citric acid solution (2×1 L), then with water (500 mL) and with brine (500 mL), dried over magnesium sulfate and concentrated in vacuo. The residues were triturated with diethyl ether and heptane to give C8 (88.11 g). A second crop of C8 was isolated from the filtrate. Combined yield: 99.83 g, 272.5 mmol, 73%. $^1$H NMR (300 MHz, CDCl$_3$) δ 1.32 (d, J=6.3 Hz, 3H), 1.47 (s, 9H), 2.79 (br dd, J=14, 14 Hz, 1H), 3.26-3.38 (br m, 1H), 3.43 (s, 3H), 3.50 (dd, half of ABX pattern, J=10.2, 4.2 Hz, 1H), 3.60 (dd, half of ABX pattern, J=10.2, 6.0 Hz, 1H), 4.41-4.62 (m, 2H), 5.45 (br d, J=5 Hz, 1H), 6.64 (dd, J=8.3, 2.5 Hz, 1H), 6.97 (d, J=2.5 Hz, 1H), 7.07 (d, J=8.2 Hz, 1H), 8.79 (br s, 1H).

Additional C8 could be isolated from the final filtrate via silica gel chromatography (Gradient: 0% to 50% EtOAc in heptane), followed by trituration with 2-propanol/heptane.

Step 7. Synthesis of Example 2. C8 (152 g, 415 mmol) was dissolved in a solution of HCl in diethyl ether (2 M, 2.5 L, 5 mol) and stirred for 18 hours, until gas evolution had ceased. The mixture was filtered to provide a solid, which was slurried in diethyl ether (4 L), filtered, and then dried overnight at 50° C. under vacuum. The solid was ground using a mortar and pestle, then further dried at 50° C. under vacuum for 18 hours to provide Example 2. Yield: 121.65 g, 401.8 mmol, 97%. LCMS m/z 267.2 (M+1). $^1$H NMR (400 MHz, D$_2$O) δ 1.21 (d, J=6.3 Hz, 3H), 3.12 (dd, half of ABX pattern, J=14.5, 14.5 Hz, 1H), 3.24 (dd, half of ABX pattern, J=14.8, 6.6 Hz, 1H), 3.35 (s, 3H), 3.57 (dd, half of ABX pattern, J=11.1, 6.5 Hz, 1H), 3.61 (dd, half of ABX pattern, J=11.1, 3.3 Hz, 1H), 4.37 (dd, J=14.5, 6.6 Hz, 1H), 4.63-4.71 (m, 1H), 6.76 (dd, J=8.4, 2.4 Hz, 1H), 6.98 (d, J=2.4 Hz, 1H), 7.21 (d, J=8.4 Hz, 1H).

Example 3

(3S)-3-Amino-1-hydroxy-7-(2-methoxyethoxy)-3,4-dihydroquinolin-2(1H)-one, HCl Salt (3)

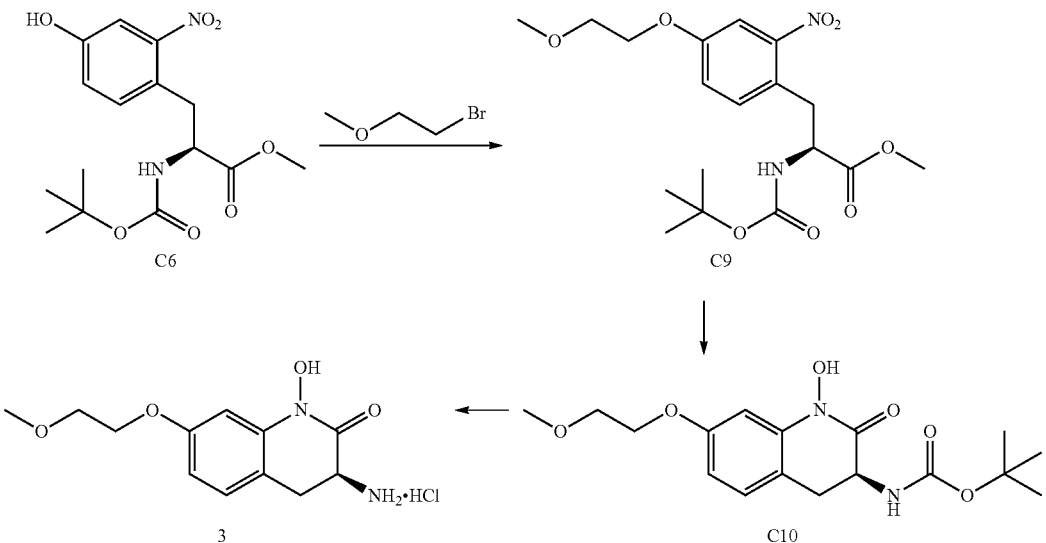

Step 1. Synthesis of methyl N-(tert-butoxycarbonyl)-O-(2-methoxyethyl)-2-nitro-L-tyrosinate (C9). 1-Bromo-2-methoxyethane (29 g, 209 mmol) was added to a mixture of C6 (48 g, 141 mmol) and cesium carbonate (115 g, 353 mmol) in N,N-dimethylformamide (240 mL). The reaction was heated to 40° C. for 5 hours, stirred at RT for 18 hours, and diluted with water (300 mL). After extraction with tert-butyl methyl ether (150 mL), the organic layers were washed with water (3×300 mL), with brine (150 mL), dried over magnesium sulfate and concentrated in vacuo to an orange oil that solidified on standing. Trituration with heptane (100 mL) and EtOAc (5 mL) provided C9 as a solid. A second crop of C9 was isolated from the filtrate. The mother liquors were concentrated under reduced pressure and triturated with 2-propanol/heptane to afford a third crop of C9. Total yield: 41.5 g, 104 mmol, 74%. $^1$H NMR (400 MHz, CDCl$_3$) δ 1.38 (s, 9H), 3.20 (dd, J=13.7, 8.2 Hz, 1H), 3.41-3.47 (m, 1H), 3.46 (s, 3H), 3.73 (s, 3H), 3.76-3.79 (m, 2H), 4.15-4.19 (m, 2H), 4.58-4.67 (m, 1H), 5.17 (br d, J=8 Hz, 1H), 7.14 (dd, J=8.6, 2.8 Hz, 1H), 7.27 (d, J=8.5 Hz, 1H), 7.50-7.54 (m, 1H).

Step 2. Synthesis of tert-butyl [(3S)-1-hydroxy-7-(2-methoxyethoxy)-2-oxo-1,2,3,4-tetrahydroquinolin-3-yl]carbamate (C10). A paste of platinum on carbon (5%, 4.50 g, 1.15 mmol) in water was added to a solution of C9 (45 g, 113 mmol) in pyridine (225 mL), and the reaction was hydrogenated at 150 psi for 18 hours at RT. The catalyst was removed by filtration through Celite, the filter pad was washed with EtOAc (250 mL) and the filtrate was concentrated in vacuo to afford an oil. Heptane (3×200 mL) was added, followed by removal of solvent under reduced pressure to drive off remaining pyridine. The resulting solid was triturated with a solution of 5% 2-propanol in heptane; filtration gave C10 as an off-white solid. The filtrate was diluted with EtOAc (50 mL), washed with 10% aqueous citric acid solution (50 mL), with water (50 mL), with brine (50 mL), dried over magnesium sulfate and concentrated in vacuo to a pale brown solid. Trituration from EtOAc/heptane afforded another crop of C10. Total yield: 27.52 g, 78.10 mmol, 69%. $^1$H NMR (400 MHz, CDCl$_3$) δ 1.45 (s, 9H), 2.79 (br dd, J=14, 14 Hz, 1H), 3.25-3.36 (br m, 1H), 3.47 (s, 3H), 3.74-3.78 (m, 2H), 4.11-4.16 (m, 2H), 4.41-4.51 (br m, 1H), 5.48 (d, J=6.0 Hz, 1H), 6.63 (dd, J=8.3, 2.5 Hz, 1H), 6.98 (d, J=2.4 Hz, 1H), 7.06 (d, J=8.4 Hz, 1H), 9.10 (br s, 1H).

Step 3. Synthesis of Example 3. C10 (29 g, 82 mmol) was combined with a solution of HCl in 1,4-dioxane (4 M, 310 mL, 1.24 mol) and stirred until a fine precipitate had formed and gas evolution had ceased (approximately 3 hours). The solid was collected by filtration, slurried in diethyl ether (150 mL), filtered and dried for 18 hours at 50° C. under vacuum. The resulting solid was slurried in refluxing methanol (300 mL) for 1 hour and filtered, and the filter cake was washed with diethyl ether. The solid was dried for 18 hours at 50° C. under vacuum to provide Example 3. Yield: 23.3 g, 80.7 mmol, 98%. LCMS m/z 253.1 (M+1). $^1$H NMR (400 MHz, D$_2$O) δ 3.10 (br dd, half of ABX pattern, J=14.7, 14.7 Hz, 1H), 3.22 (br dd, half of ABX pattern, J=15, 6.5 Hz, 1H), 3.37 (s, 3H), 3.74-3.79 (m, 2H), 4.13-4.18 (m, 2H), 4.31-4.38 (m, 1H), 6.73 (dd, J=8.4, 2.5 Hz, 1H), 6.97 (d, J=2.6 Hz, 1H), 7.21 (d, J=8.4 Hz, 1 H).

Example 4

(3S)-3-Amino-1-hydroxy-3,4-dihydroquinolin-2(1H)-one (4)

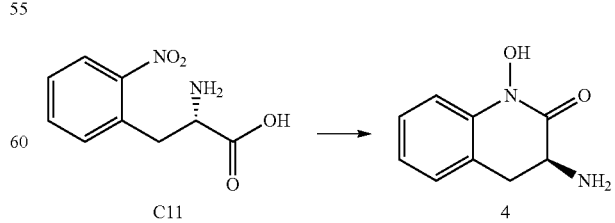

L-2-Nitrophenylalanine (C11) (419.6 mg, 2.0 mmol) was dissolved in methanol (23.8 mL) and water (240 μL). Concentrated aqueous HCl (2-4 drops) was added to aid solubility. Platinum on carbon (42 mg) was added and the reaction was hydrogenated on a Parr shaker at 10 psi for 1 hour, whereupon the reaction was filtered through Celite. The catalyst was washed with a 1 N solution of ammonium hydroxide in methanol and then with methanol. The filtrate was concentrated to provide a crude product, which was subsequently dry packed with a minimum amount of silica, using a methanol/dichloromethane solution to dissolve the material. Purification using silica gel chromatography (Gradient: 0% to 20% methanol (containing 1% ammonium hydroxide) in dichloromethane) provided Example 4 as a solid (207 mg, 58%).

APCI m/z 179.1 (M+1). $^1$H NMR (400 MHz, CD$_3$OD) δ 2.88 (dd, J=14, 15 Hz, 1H), 3.09 (dd, J=15.3, 6.2 Hz, 1H), 3.67 (dd, J=13.6, 6.1 Hz, 1H,) 7.06 (ddd, J=7.2, 7.2, 1.7 Hz, 1H), 7.23 (br d, J=7.5 Hz, 1H), 7.27-7.34 (m, 2H).

Example 5

(3S)-3-Amino-1-hydroxy-7-isopropoxy-3,4-dihydroquinolin-2(1H)-one, HCl Salt (5)

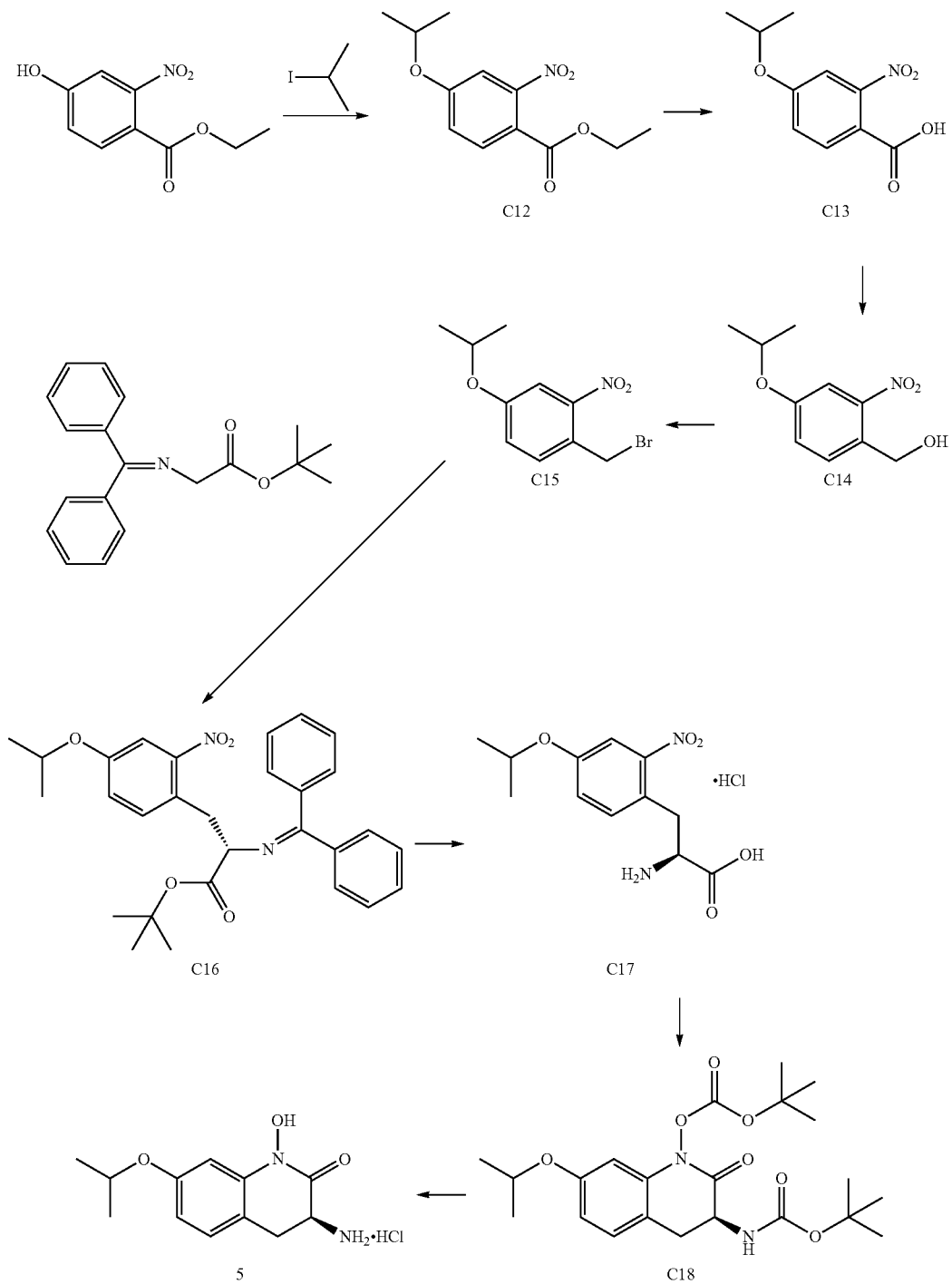

Step 1. Synthesis of ethyl 4-isopropoxy-2-nitrobenzoate (C12). A mixture of ethyl 4-hydroxy-2-nitrobenzoate (1.02 g, 4.83 mmol) and potassium carbonate (1.3 g, 9.4 mmol) in N,N-dimethylformamide (20 mL) was treated with 2-iodopropane (0.54 mL, 5.4 mmol), and the reaction mixture was allowed to stir for 18 hours. The reaction was poured into water and acidified with 1 N aqueous HCl. After extraction with EtOAc, the combined organic layers were washed with water, then with brine, dried over magnesium sulfate, filtered and concentrated in vacuo to provide C12 as an oil. Yield: 1.17 g, 4.62 mmol, 96%. $^1$H NMR (400 MHz, $CDCl_3$) δ 1.34 (t, J=7.1 Hz, 3H), 1.38 (d, J=6.0 Hz, 6H), 4.34 (q, J=7.1 Hz, 2H), 4.64 (septet, J=6.0 Hz, 1H), 7.06 (dd, J=8.7, 2.5 Hz, 1H), 7.20 (d, J=2.4 Hz, 1H), 7.77 (d, J=8.7 Hz, 1H).

Step 2. Synthesis of 4-isopropoxy-2-nitrobenzoic acid (C13). Aqueous lithium hydroxide solution (1 M, 6.93 mL, 6.93 mmol) was added to a solution of C12 (1.17 g, 4.62 mmol) in tetrahydrofuran (10 mL) and methanol (10 mL), and the reaction was allowed to stir at RT for 3 hours. The reaction was then poured into 1 N aqueous HCl and extracted with diethyl ether. The combined organic layers were washed with water, then with brine, dried over magnesium sulfate, filtered and concentrated in vacuo to provide C13 as an orange solid. Yield: 847 mg, 3.76 mmol, 81%. $^1$H NMR (400 MHz, $CDCl_3$) δ 1.40 (d, J=6.0 Hz, 6H), 4.67 (septet, J=6.0 Hz, 1H), 7.07 (dd, J=8.8, 2.4 Hz, 1H), 7.12 (d, J=2.4 Hz, 1H), 7.94 (d, J=8.8 Hz, 1H).

Step 3. Synthesis of (4-isopropoxy-2-nitrophenyl)methanol (C14). To a solution of C13 (845 mg, 3.75 mmol) in tetrahydrofuran (15 mL) was added borane-tetrahydrofuran complex (1 M solution in tetrahydrofuran, 15.0 mL, 15.0 mmol), and the reaction was heated at 50° C. for 18 hours. The reaction was slowly added to water (75 mL), then extracted with EtOAc. The combined organic layers were washed with 0.5 N aqueous HCl, with water, and with brine, then dried over magnesium sulfate, filtered and concentrated in vacuo. C14 was obtained as a yellow oil. Yield: 550 mg, 2.60 mmol, 69%. LCMS m/z 210.1 (M−1). $^1$H NMR (400 MHz, $CDCl_3$) δ 1.38 (d, J=6.0 Hz, 6H), 2.59 (br t, J=6 Hz, 1H), 4.63 (septet, J=6.0 Hz, 1H), 4.85 (br d, J=5.9 Hz, 2H), 7.16 (dd, J=8.5, 2.7 Hz, 1H), 7.56 (br d, J=8.5 Hz, 1H), 7.59 (d, J=2.6 Hz, 1H).

Step 4. Synthesis of 1-(bromomethyl)-4-isopropoxy-2-nitrobenzene (C15). A solution of C14 (550 mg, 2.60 mmol) in diethyl ether (50 mL) was cooled to 0° C. and treated dropwise with phosphorus tribromide (0.245 mL, 2.61 mmol). The reaction was stirred at 0° C. for 2.5 hours, then at RT for 3 hours. The supernatant was decanted away from an insoluble oil at the bottom of the flask, and the supernatant was diluted with additional diethyl ether and washed with water, then with brine, dried over magnesium sulfate, filtered and concentrated in vacuo. The residue was purified via silica gel chromatography (Gradient: 10% to 20% EtOAc in heptane) to provide C15 as a colorless oil. Yield: 245 mg, 0.894 mmol, 34%. $^1$H NMR (400 MHz, $CDCl_3$) δ 1.38 (d, J=6.0 Hz, 6H), 4.62 (septet, J=6.0 Hz, 1 H), 4.80 (s, 2H), 7.09 (dd, J=8.5, 2.6 Hz, 1H), 7.44 (d, J=8.6 Hz, 1H), 7.54 (d, J=2.6 Hz, 1H).

Step 5. Synthesis of tert-butyl N-(diphenylmethylene)-O-isopropyl-2-nitro-L-tyrosinate (C16). C15 (245 mg, 0.894 mmol), tert-butyl N-(diphenylmethylene)glycinate (290 mg, 0.982 mmol) and O-allyl-N-(9-anthracenylmethyl)cinchonidinium bromide (53.9 mg, 0.089 mmol) were combined in dichloromethane (5 mL) and cooled to −30° C. (see E. J. Corey et al., *J. Am. Chem. Soc.* 1997, 119, 12414-12415). Cesium hydroxide (225 mg, 1.34 mmol) was added and the reaction was allowed to stir at −30° C. for 18 hours, at which time it was quenched with saturated aqueous ammonium chloride solution, and extracted with dichloromethane. The combined organic layers were washed with water, with brine and dried over magnesium sulfate. After filtration, the organic solution was concentrated in vacuo and purified by silica gel chromatography (Gradient: 10% to 20% EtOAc in heptane) to afford C16 as a pale yellow oil. Yield: 252 mg, 0.516 mmol, 58%. $^1$H NMR (400 MHz, $CDCl_3$) δ 1.33 (d, J=6.0 Hz, 3H), 1.34 (d, J=6.0 Hz, 3H), 1.44 (s, 9H), 3.32 (dd, J=13.5, 9.2 Hz, 1H), 3.61 (dd, J=13.6, 4.1 Hz, 1H), 4.30 (dd, J=9.2, 4.1 Hz, 1H), 4.55 (septet, J=6.0 Hz, 1H), 6.67 (br d, J=6.9 Hz, 2H), 6.96 (dd, J=8.5, 2.7 Hz, 1H), 7.24-7.40 (m, 8H), 7.57-7.60 (m, 2H).

Step 6. Synthesis of O-isopropyl-2-nitro-L-tyrosine, HCl salt (C17). A solution of C16 (252 mg, 0.516 mmol) in tetrahydrofuran (5 mL) was treated with aqueous HCl (6 M, 1.83 mL, 11.0 mmol). After stirring for 18 hours, the reaction was concentrated in vacuo. The residue was slurried with diethyl ether and filtered to provide C17 as a colorless solid. Yield: 150 mg, 0.492 mmol, 95%. LCMS m/z 269.2 (M+1). $^1$H NMR (400 MHz, $CD_3OD$), characteristic peaks: δ 1.35 (d, J=6.0 Hz, 6H), 3.57 (dd, J=14.1, 7.0 Hz, 1H), 4.29 (dd, J=7.8, 7.1 Hz, 1H), 4.71 (septet, J=6.0 Hz, 1H), 7.25 (dd, J=8.5, 2.7 Hz, 1H), 7.40 (d, J=8.6 Hz, 1H), 7.60 (d, J=2.6 Hz, 1H).

Step 7. Synthesis of tert-butyl {(3S)-1-[(tert-butoxycarbonyl)oxy]-7-isopropoxy-2-oxo-1,2,3,4-tetrahydroquinolin-3-yl}carbamate (C18). C17 (150 mg, 0.492 mmol) was mixed with THF (10 mL) and MeOH (10 mL), and the resulting solution was cooled to 0° C. To this was added tin(II) chloride (97%, 494 mg, 2.53 mmol) and sodium acetate trihydrate (99%, 694 mg, 5.05 mmol), and the reaction was allowed to stir at 0° C. for 5 hours. At that time, triethylamine (0.704 mL, 5.05 mmol) and di-tert-butyl dicarbonate (220 mg, 1.01 mmol) were added and the mixture was stirred at room temperature for 18 hours. Solvents were removed in vacuo, and the residue was slurried with EtOAc. The mixture was filtered, and the insoluble solids were washed with EtOAc. The combined filtrates were washed with water and with brine, dried over magnesium sulfate, filtered and concentrated under reduced pressure. The residue was purified using silica gel chromatography (Gradient: 10% to 30% EtOAc in heptane, with 1% triethylamine added) to provide C18 as a colorless oil. Yield: 92 mg, 0.21 mmol, 43%. LCMS m/z 437.2 (M+1). $^1$H NMR (400 MHz, $CDCl_3$) δ 1.33 (d, J=6 Hz, 6H), 1.47 (s, 9H), 1.56 (s, 9H), 2.81-2.95 (m, 1H), 3.32-3.44 (m, 1H), 4.46-4.57 (m, 2H), 5.55 (br s, 1H), 6.60 (d, J=8 Hz, 1H), 7.11 (d, J=8 Hz, 1H), 7.27 (s, 1H).

Step 8. Synthesis of Example 5. A solution of C18 (92 mg, 0.21 mmol) in methanol (5 mL) was treated with concentrated aqueous HCl (12 M, 0.158 mL, 1.90 mmol) and heated to 50° C. for 1 hour. The reaction mixture was concentrated in vacuo, and the resulting solid was slurried in diethyl ether, then collected via filtration. The solid was washed with diethyl ether to afford Example 5. Yield: 49 mg, 0.18 mmol, 86%. LCMS m/z 237.2 (M+1). $^1$H NMR (400 MHz, $CD_3OD$) δ 1.32 (d, J=6.0 Hz, 6H), 3.06 (ddd, J=14.6, 14.6, 1.1 Hz, 1H), 3.19 (dd, J=14.6, 6.5 Hz, 1H), 4.29 (dd, J=14.6, 6.5 Hz, 1H), 4.61 (septet, J=6.0 Hz, 1H), 6.67 (dd, J=8.3, 2.5 Hz, 1H), 6.93 (d, J=2.4 Hz, 1H), 7.18 (br d, J=8.3 Hz, 1H).

Example 6

3-Amino-1-hydroxy-2-oxo-1,2,3,4-tetrahydroquinoline-8-carbonitrile, HCl Salt (6)

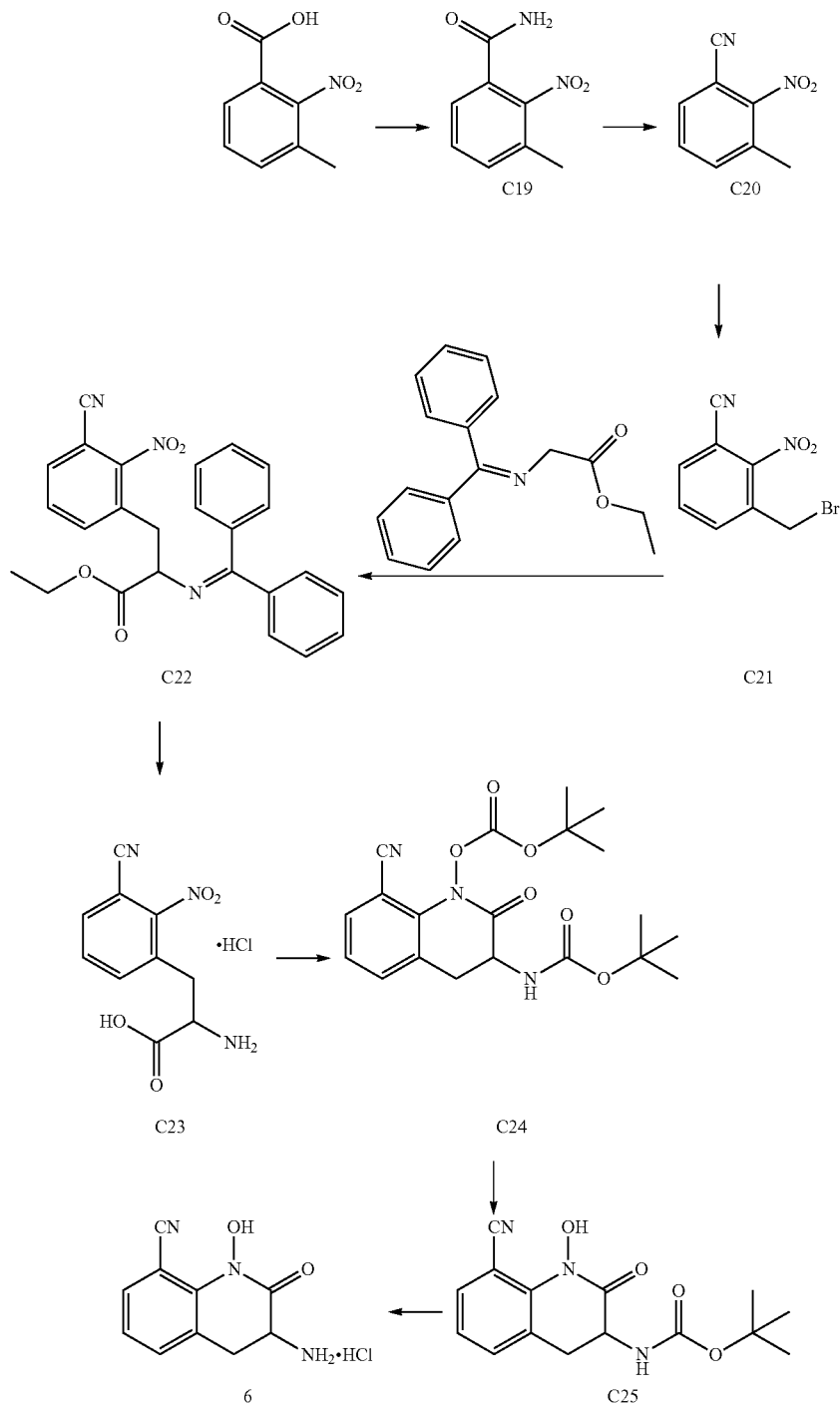

Step 1. Synthesis of 3-methyl-2-nitrobenzamide (C19). A solution of 3-methyl-2-nitrobenzoic acid (50.00 g, 276 mmol) in dichloromethane (500 mL) and triethylamine (41.83 g, 414 mmol) was cooled to 0° C. Isopropyl chloroformate (50.74 g, 414 mmol) was added drop-wise and the reaction was stirred for 1 hour at 0° C.

Concentrated aqueous ammonium hydroxide (300 mL) was then added to the reaction, which was stirred for an additional 30 minutes at 0° C. Filtration afforded C19 as a white solid. Yield: 41.6 g, 231 mmol, 84%. $^1$H NMR (400 MHz, DMSO-$d_6$) δ 2.28 (s, 3H), 7.53-7.61 (m, 3H), 7.71 (br s, 1H), 8.21 (br s, 1H).

Step 2. Synthesis of 3-methyl-2-nitrobenzonitrile (C20). A solution of C19 (41.60 g, 231 mmol) in dichloromethane (400 mL) was cooled to 0° C. Trifluoroacetic anhydride (96.6 g, 460 mmol) was added drop-wise, and the resulting mixture was stirred for 1 hour at 0° C., then washed with water (400 mL). The organic layer was dried over anhydrous magnesium sulfate, filtered and concentrated in vacuo. The residue was purified via silica gel chromatography (Eluants: 8:1, then 4:1 petroleum ether/ethyl acetate) to provide C20 as a yellow solid. Yield: 25 g, 150 mmol, 65%. $^1$H NMR (400 MHz, CDCl$_3$) δ 2.42 (s, 3H), 7.49-7.56 (m, 2H), 7.61-7.63 (m, 1H).

Step 3. Synthesis of 3-(bromomethyl)-2-nitrobenzonitrile (C21). A mixture of C20 (15.00 g, 92.51 mmol), N-bromosuccinimide (32.93 g, 185.0 mmol), and benzoyl peroxide (3.36 g, 13.9 mmol) in carbon tetrachloride (200 mL) was heated at reflux for 48 hours. The mixture was washed with water (100 mL), and the organic layer was dried, filtered and purified on a silica gel column (Eluants: 2:1 to 1:1 petroleum ether/dichloromethane) to afford C21 as an off-white solid. Yield: 6.26 g, 26.0 mmol, 28%. $^1$H NMR (400 MHz, CDCl$_3$) δ 4.60 (s, 2H), 7.67-7.71 (m, 1H), 7.80-7.85 (m, 2H).

Step 4. Synthesis of ethyl 3-cyano-N-(diphenylmethylene)-2-nitrophenylalaninate (C22). To a solution of ethyl N-(diphenylmethylene)glycinate (5.00 g, 18.7 mmol) in N,N-dimethylformamide (50 mL) at 0° C. was carefully added sodium hydride (60% in oil, 900 mg, 22.4 mmol) and the mixture was stirred at 0° C. for 1 hour. C21 (4.51 g, 18.7 mmol) was added in one portion to the cold mixture and the reaction was stirred for 30 minutes at 0° C. The reaction was quenched with water (100 mL) and the mixture was extracted with ethyl acetate (2×100 mL). The combined organic layers were washed with brine (2×50 mL), dried, filtered and concentrated in vacuo. Purification via silica gel chromatography (Eluants: 6:1 to 4:1 petroleum ether/ethyl acetate) provided C22 as a brown oil. Yield: 4.5 g, 10.5 mmol, 56%. $^1$H NMR (400 MHz, CDCl$_3$) δ 1.16-1.20 (t, 3H), 3.24 -3.44 (m, 2H), 4.02-4.19 (m, 2H), 4.31-4.37 (m, 1H), 6.59-6.69 (m, 2H), 7.24-7.38 (m, 6H), 7.39-7.42 (m, 1H), 7.49-7.51 (d, 2H), 7.56-7.71 (m, 2H).

Step 5. Synthesis of 3-cyano-2-nitrophenylalanine, HCl salt (C23). To C22 (2.00 g, 4.68 mmol) was added concentrated aqueous HCl (20 mL) at RT, and the reaction was heated at 50° C. for 42 hours. The resulting mixture was concentrated in vacuo and the residue was washed with ethyl acetate (25 mL) and filtered to afford C23 as a yellow solid. Yield: 1.08 g, 3.98 mmol, 85%.

Step 6. Synthesis of tert-butyl {1-[(tert-butoxycarbonyl)oxy]-8-cyano-2-oxo-1,2,3,4-tetrahydroquinolin-3-yl}carbamate (C24). Compound C23 was converted to C24 according to the general procedure for the transformation of C17 to C18 in Example 5. C24 was obtained as a yellow solid. Yield: 300 mg, 0.744 mmol, 19%. $^1$H NMR (400 MHz, CDCl$_3$) δ 1.39-1.40 (m, 9H), 1.49-1.55 (m, 9H), 2.87-2.98 (br m, 1H), 3.30-3.51 (br m, 1H), 4.40-4.60 (br m, 1H), 5.55 (br m, 1H), 7.09-7.14 (m, 1H), 7.37-7.39 (m, 1H), 7.52-7.54 (d, 1H).

Step 7. Synthesis of tert-butyl (8-cyano-1-hydroxy-2-oxo-1,2,3,4-tetrahydroquinolin-3-yl)carbamate (C25). Acetic acid (0.2 mL) was added to a solution of C24 (210 mg, 0.52 mmol) in tetrahydrofuran (5 mL) and water (5 mL), and the reaction was stirred at 50° C. for 5 hours. After concentration in vacuo, the aqueous residue was extracted with ethyl acetate (10 mL). The organic layer was dried, filtered and purified by preparative thin layer chromatography, providing C25 as a yellow solid. Yield: 140 mg, 0.46 mmol, 88%. $^1$H NMR (400 MHz, CDCl$_3$) δ 1.39 (s, 9H), 2.82-2.89 (m, 1H), 3.30-3.38 (br m, 1H), 4.44-4.47 (br m, 1H), 5.43 (m, 1H), 7.05-7.12 (m, 1H), 7.34-7.36 (d, 1H), 7.54-7.56 (d, 1H).

Step 8. Synthesis of Example 6. C25 (140 mg, 0.46 mmol) was treated with a solution of HCl in 1,4-dioxane (6 N, 15 mL) and the reaction mixture was stirred for 6 hours at RT. Diethyl ether (30 mL) was slowly added, and the mixture was stirred for 30 minutes, then allowed to stand for 1 hour. The precipitate was collected by filtration, affording Example 6 as an off-white solid. Yield: 48 mg, 0.20 mmol, 43%. LCMS m/z 204.4 (M+1). $^1$H NMR (400 MHz, DMSO-d$_6$) δ 3.16 (dd, J=15, 15 Hz, 1H), 3.27 (dd, J=15, 6 Hz, 1H), 4.47 (dd, J=14.6, 6.3 Hz, 1H), 7.23 (dd, J=7.6, 7.6 Hz, 1H), 7.65 (d, J=7.3 Hz, 1H), 7.74 (d, J=7.7 Hz, 1H), 8.76 (br s, 3H), 11.5 (v br s, 1H).

Human KAT II Inhibition Spectra Assay

Formation of kynurenic acid (KYNA) is indirectly assessed by a decrease in light absorbance at 370 nm (OD370) as the L-kynurenine (KYN) substrate is converted by the human KAT II (hKAT II) enzyme into KYNA. An inhibitor would therefore inhibit the decrease in OD370.

The protocol was performed by placing the following reagents into a Costar 384 well black plate (30 µL total assay volume/well):
- 10 µL of 3× concentrated compound;
- 10 µL of 3× concentrated substrate mix (BGG (Sigma G-5009); 3 mM L-Kynurenine in 150 mM Tris Acetate (Sigma K3750); 3 mM α-ketoglutaric acid in 150 mM Tris Acetate (Sigma K2010); and 210 µM pyridoxal 5-phosphate (PLP) in 150 mM Tris Acetate (Sigma 9255)); and
- 10 µL of 3× concentrated enzyme (15 nM enzyme in 150 mM Tris Acetate with 0.3% bovine serum).

Plates were sealed and incubated at 37° C. for 15-20 h before reading OD370 on a SpectraMax Plus plate reader. IC$_{50}$s were generated by comparing the efficacy of compounds across a concentration range to inhibit a reduction in the OD370 value relative to assay wells with DMSO added in place of concentrated compound. Biological data for the Examples may be found Tables 1 and 2.

The compounds of the present invention are irreversible inhibitors of KATII. Potency of irreversible inhibitors is best characterized by kinact/KI (See Copeland, R. A.; "Evaluation of Enzyme Inhibitors in Drug Discovery," Wiley, 2005).

KATII Kinetic Assay

Test compounds were dissolved in 100% DMSO and diluted to the required concentrations in 100% DMSO. An additional aqueous dilution was made so that the compound at 3× final concentration was 1.0% DMSO in the assay specific buffer. Compounds were tested at 11 concentrations. Final DMSO concentrations in the assay plate were equal to 0.33%.

Assay Methodology

KATII enzyme activity was followed by measuring the loss of absorbance of the L-KYN substrate at an absorbance wavelength of 370 nm. The KATII assays were run in a 384 well format at a final volume of 30 µL using 150 mM Tris Acetate buffer (pH7.0), 1 mM L-KYN,1 mM α-ketoglutaric acid, 70 µM PLP, 0.1% BGG and either 30 nM human KATII enzyme or 5 nM rat KATII enzyme KATII enzyme. Compound was diluted in 100% DMSO and spotted prior to the addition of the other reagents. Enzyme was always added last. Assay plates were sealed around the edges with tape and immediately read on a SpectraMax plate reader at an absorbance wavelength of 370 nm. The SpectraMax plate reader was set up to read every 5 min for 16 hours.

The following steps are taken to ensure consistent production of kinetic read data:
1. A 10 µL aliquot of the compound dilutions (described above in compound preparation) was added to the assay plate by hand followed by a quick spin to ensure compound was collected at bottom of well.

2. A 10 µL aliquot of substrate mix containing the L-KYN, a-ketoglutaric acid and PLP was then added to the assay plate via a Multidrop instrument.
3. Finally, a 10 µL aliquot of a 3× concentration of enzyme stock soluton was added last to initiate the reaction via a Multidrop instrument.
4. The microplate lid was placed onto the assay plate and taped to seal in humidity, and the assay plate was put into the SpectraMax reader. A quick vibration on the plate platform was done to ensure mixing, and the absorbance was read (wavelength of 370 nm) every 5 min over 16 h at room temperature.

Determination of Potencies ($k_{inact}/K_I$ Values)

The direct substrate absorbance loss assay described above was performed for the determination of potencies ($k_{inact}/K_I$ values). The overall potency, $k_{inact}/K_1$ values, were determined using the general approach described by M. Mileni et al., *Proc. Natl. Acad. Sci. USA* 2008, 105 12820-12824 and K. Ahn et al. *Chem. Biol.* 2009, 16, 411-420. Reaction progress curves (decrease in A370 nm with time) were obtained in the presence of eleven concentrations of inhibitor with top dose at 1 mM and diluted by 2 fold to 1 nM. A null inhibitor control is always included. Absorbance read data were collected for 16 hours at 5 minute intervals. Data analysis was performed using GraphPad Prism version 5.01 for Windows, GraphPad Software, San Diego, Calif. USA. Each progress curve was fit to a one phase exponential decay model (equation 1) to determine $k_{observed}$ ($k_{obs}$) values at each inhibitor concentration, where $A_t$ is absorbance at time t, $A_0$ is the absorbance at t=infinite, $A_1$ is a total absorbance change (the absorbance difference between t=0 and t=infinite), and $k_{obs}$ is the first order rate constant for enzyme inactivation. For the human KATII enzyme, a 6 hour time window (5 minutes to 360 minutes) was used to derive the $k_{obs}$ value across all inhibitor concentrations. The inhibitor dissociation constant ($K_I$) and the first-order rate constant of enzyme inactivation at infinite inhibitor concentration ($k_{inact}$) were then obtained by fitting the $k_{obs}$ vs. [I] curves to equation 2. When [I]<<$K_1$, equation 2 is simplified to equation 3, where the $k_{inact}/K_I$ is calculated from the slope, $k_{inact}/[K_I(1+[S]/K_m)]$, which is obtained from the $k_{obs}$ vs [I] linear regression fit.

$$A_t = A_0 + A_1 e^{-k_{obs} t} \quad (1)$$

$$k_{obs} = \frac{k_{inact}[I]}{[I] + K_I\left(1 + \frac{[S]}{K_m}\right)} \quad (2)$$

$$k_{obs} = \frac{k_{inact}}{K_I\left(1 + \frac{[S]}{K_m}\right)}[I] \quad (3)$$

Reactive Metabolite Assay Protocol

Metabolite activity in Table 2 is measured using a reactive metabolite assay protocol as described in Reactive Metabolite assay protocol: See J. R. Soglia et al., *J. Pharm. Biomed. Anal.* 2004, 36, 105-116.

Human Hepatocyte Assay (HHEP)

Human hepatocyte assay (HHEP) is an vitro system used to monitor hepatic metabolism since these intact cells contain all the hepatic enzymes found in vivo, including phase I enzymes (such as CYPs, aldehyde oxidases and MAOs) and phase II enzymes (such as UDP-glucuronyltransferases and sulfotransfereases). The purpose of this assay is to rank compounds based on apparent in vitro intrinsic clearance ($CL_{int, app}$).

The protocol was performed by using either of the following media:

a. Invitrogen custom powder, which is supplemented with 292 mg/mL L-glutamine without phenol red. 2.2 g/L of $NaHCO_3$ must be added prior to use. The media is gassed with 95/5 $O_2/CO_2$ (or air/$CO_2$) for 20-30 minutes. The pH is adjusted to 7.4, and warmed to 37° C. Alternatively, if incubations will not be conducted in $CO_2$ incubators, gassing of media is omitted and HEPES is added to a final concentration of 50 mM in 37° C. media and pH is adjusted to 7.4. The media is then filtered sterilized.

b. Invitrogen custom 1× liquid, which is supplemented with 24 mM $NaHCO_3$ and 50 mM HEPES without phenol red. 292 mg/mL L-glutamine must be added prior to use. The media is warmed to 37° C.

c. Invitrogen custom 1× liquid, which is supplemented with 24 mM $NaHCO_3$ and without phenol red. 292 mg/mL L-glutamine must be added prior to use. The media is gassed with 95/5 $O_2/CO_2$ (or air/$CO_2$) for 20-30 minutes, and pH adjusted to 7.4. The media is warmed to 37° C.

The $CO_2$ incubator settings are set to 95/5 air/$CO_2$, 37° C., and 95% humidity. The incubations are conducted in 96-well or 384-well flat bottom plates.

a. Preparation of Test Compounds (Substrates)

Test compound stocks are diluted in DMSO such that the final DMSO concentration in the hepatocyte incubation is ≤0.1%. The final test compound concentration is 1 µM. Incubation concentrations for the three required positive controls (initially dissolved in DMSO): 0.1 µM Propranolol, 1.0 µM Midazolam, 1.0 µM Naloxone.

b. Thawing Procedure for IVT Cryopreserved Hepatocytes

Cryopreserved hepatocytes are prepared in multiples of 5 donors. Vials are thawed in a 37-40° C. water bath until ice is almost all melted for 75-90 seconds. Vial contents are emptied into a conical tube or flask. The cells are resuspended by gentle inversion. The cells are centrifuged at 50-90 g at room temperature for 5 min. The supernatant is discarded. WEM is added and the tube is inverted gently to resuspend the hepatocytes. The total cell count and the number of viable cells are determined by using the Trypan Blue exclusion method. The cell pellet is resuspended in WEM to achieve the desired density of cells prior to dispensing the cells into plates.

c. Incubation Conditions 96 or 384 well plates are used. The temperature is set at 37° C. and the $CO_2$ incubator is set at 95/5 air: $CO_2$ at 95% humidity. The hepatocyte density is 0.5 million viable cells/mL. Minimum initial hepatocyte viability (based on TBE) is 70% Initial viability can be increased by Percoll centrifugation if desired. Final incubation volumes are less than or equal to 50 µL for 96-well plates, and less than or equal to 20 µL for 384-well plates. The final DMSO concentration in the incubation cannot exceed 0.1%.

d. Assay Criteria and Calculations

At least five sampling time points must be taken that include 30, 60, 90 and 120 minutes, but should not exceed 240 minutes. The criteria for reportable data is that the regression line must have an $r^2$ of greater than or equal to 0.85 in order to report in vitro $CL_{int}$.

e. Equation $$CL_{int, app} = [-slope/0.5 \text{ M cells/mL}] \cdot 1000 \text{ µL/mL} = \text{µL/min/M cells} \quad a.$$

The results of are given in Tables 1 and 2.

TABLE 1

| Ex# | hKATII IC$_{50}$ (nM) | hKATII k$_{inact}$/K$_I$ (M$^{-1}$s$^{-1}$) | HHEP CL$_{int, app}$ (μL/min/million) |
|---|---|---|---|
| 1 | 19 | 46,200 (n = 8) | 24.8 |
| 4 | 27 | 21,500 (n = 10) | 39.6 |
| 6 | 30 | — | — |

TABLE 2

| Ex# | hKATII IC$_{50}$ (nM) | hKATII k$_{inact}$/K$_I$ (M$^{-1}$s$^{-1}$) | Reactive Metabolite Formation | HHEP CL$_{int, app}$ (μL/min/million) |
|---|---|---|---|---|
| 3 | 22 | 22,300 (n = 4) | No | 30.1 |
| 2 | 18 | 25,100 (n = 4) | No | 19.8 |
| 5 | 32 | 17,100 (n = 2) | Yes | 44.7 |

Pharmacokinetics Studies in Dog

Test substances (Examples 2-3) were administered by oral gavage or IV administration to groups of two dogs. The two male dogs were beagles obtained from Marshal Farms, weighing from about 9 to about 12 kg at start of treatment and ranging in age between approximately 4 to approximately 6 years.

Blood samples were taken times of 0.25, 0.5, 1, 2, 4, 7, and 24 h after administration and submitted to analysis for the drug substance using an LC-MS-MS assay. Pharmacokinetic parameters derived from the plasma analytical data were determined using Watson 7.2.003. The results are given in Table 3 and Table 4.

TABLE 3

Pharmacokinetics of Examples 2, 3 and 5 in dogs after oral administration

| Ex# | Dose (mg/kg) | Cmax (ng/mL) | T$_{1/2}$ (h) | AUC (ng*h/mL) | AUC/dose | C$_{max}$/dose |
|---|---|---|---|---|---|---|
| 3 | 5 | 198 | 1.05 | 156 | 31.2 | 39.6 |
| 2 | 5 | 229 | 2.28 | 195 | 39 | 46 |
| 5 | 2 | 19.6 | 0.46 | 18.6 | 9.3 | 9.8 |

TABLE 4

Pharmacokinetics of Compounds 2 and 3 and Example 5 in dogs after IV administration (dose = 0.5 mg/kg)

| Ex# | C$_0$ (ng/mL) | T$_{1/2}$ (h) | AUC (ng * h/mL) | AUC/dose | CL (mL/min/kg) |
|---|---|---|---|---|---|
| 3 | 446 | 0.9 | 194 | 388 | 43.4 |
| 2 | 352 | 0.5 | 185 | 370 | 44.9 |
| 5 | 265 | 0.6 | 218 | 436 | 38.7 |

When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements.

Although this invention has been described with respect to specific embodiments, the details of these embodiments are not to be construed as limitations to the invention, the scope of which is defined by the appended claims.

The invention claimed is:

1. A compound of Formula I, IA, IB, IIB, III, IIIA, or IIIB:

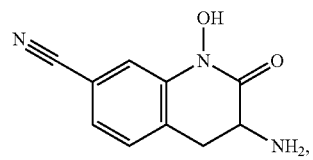

I

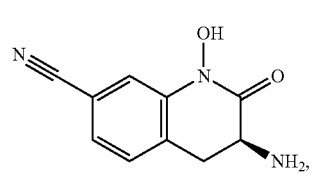

IA

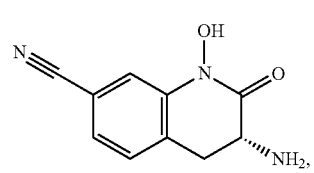

IB

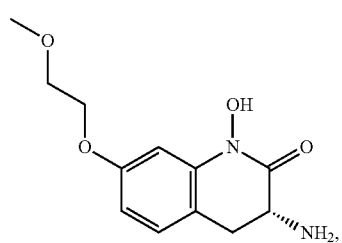

IIB

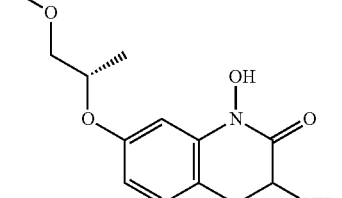

III

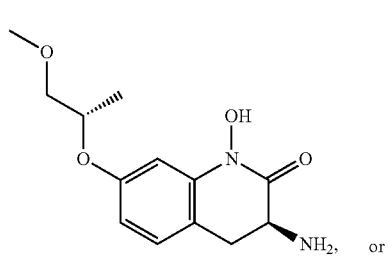

IIIA or

-continued

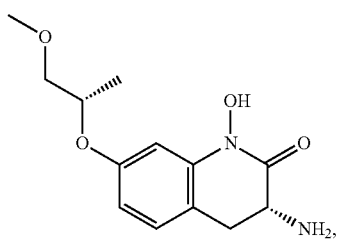
IIIB or a pharmaceutically acceptable salt thereof.

2. The compound of claim 1 wherein the compound is a compound of Formula I, IA, or IB:

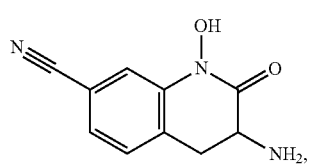
I

IA

IB or a pharmaceutically acceptable salt thereof.

3. A compound of Formula IA:

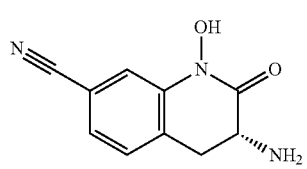
IA or a pharmaceutically acceptable salt thereof.

4. The compound of claim 3, wherein the compound has at least 95% ee, or a pharmaceutically acceptable salt thereof.

5. The compound of claim 3, wherein the compound has at least 99% ee, or a pharmaceutically acceptable salt thereof.

6. The compound of claim 1 wherein the compound is a compound of Formula IIB:

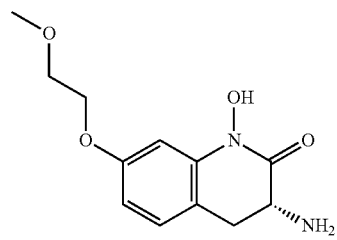
IIB or a pharmaceutically acceptable salt thereof.

7. A compound of Formula IIA

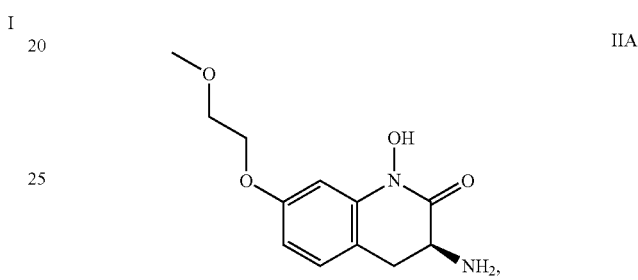
IIA wherein the compound has at least 95% ee, or a pharmaceutically acceptable salt thereof.

8. The compound of claim 7, wherein the compound has at least 99% ee, or a pharmaceutically acceptable salt thereof.

9. The compound of claim 1 wherein the compound is a compound of Formula III, IIIA, or IIIB:

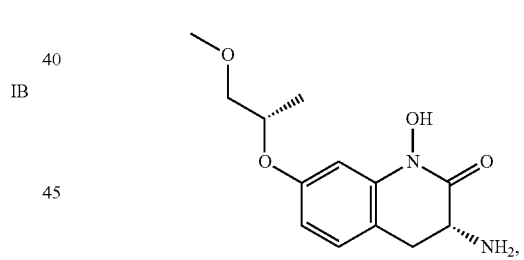
III

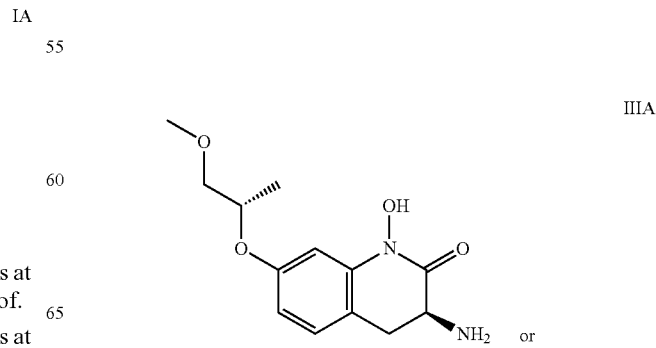
IIIA

-continued

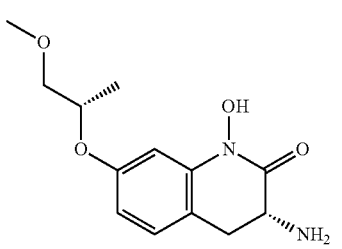

IIIB or a pharmaceutically acceptable salt thereof.

10. The compound of claim 9, wherein the compound is a compound of Formula IIIA, or a pharmaceutically acceptable salt thereof.

11. The compound of claim 10, wherein the compound has at least 95% ee, or a pharmaceutically acceptable salt thereof.

12. The compound of claim 10, wherein the compound has at least 99% ee, or a pharmaceutically acceptable salt thereof.

13. A pharmaceutical composition comprising a compound of claim 1, or a pharmaceutically acceptable salt thereof, and a pharmaceutically acceptable carrier.

14. A pharmaceutical composition comprising a compound of claim 2, or a pharmaceutically acceptable salt thereof, and a pharmaceutically acceptable carrier.

15. A pharmaceutical composition comprising a compound of claim 3, or a pharmaceutically acceptable salt thereof, and a pharmaceutically acceptable carrier.

16. A pharmaceutical composition comprising a compound of claim 9, or a pharmaceutically acceptable salt thereof, and a pharmaceutically acceptable carrier.

* * * * *